United States Patent
Nerney (10) Patent No.: US 7,118,556 B2
(45) Date of Patent: Oct. 10, 2006

(54) FORWARD-MOUNTED PLUNGER CONTROL FOR RETROFIT ATTACHMENT TO AN EXISTING SYRINGE

(76) Inventor: Michael E. Nerney, 12408 Chickasaw Trail, Largo, FL (US) 33774

( * ) Notice: Subject to any disclaimer, the term of this patent is extended or adjusted under 35 U.S.C. 154(b) by 110 days.

(21) Appl. No.: 10/708,745

(22) Filed: Mar. 23, 2004

(65) Prior Publication Data
US 2005/0215956 A1   Sep. 29, 2005

(51) Int. Cl.
*A61M 5/315* (2006.01)

(52) U.S. Cl. .................. 604/227; 604/218; 604/181

(58) Field of Classification Search ............... 604/218, 604/227–229, 220, 207–208, 116–118, 181, 604/187, 223
See application file for complete search history.

(56) References Cited

U.S. PATENT DOCUMENTS

| | | | | |
|---|---|---|---|---|
| 3,325,061 A | * | 6/1967 | Ellsworth | 222/386 |
| 3,819,091 A | * | 6/1974 | Hollender | 222/327 |
| 4,687,472 A | * | 8/1987 | Gross | 604/223 |
| 5,115,816 A | * | 5/1992 | Lee | 600/562 |
| 5,135,511 A | * | 8/1992 | Houghton et al. | 604/220 |
| 5,582,595 A | * | 12/1996 | Haber et al. | 604/187 |
| 5,814,023 A | * | 9/1998 | Fulk et al. | 604/232 |
| 5,830,152 A | * | 11/1998 | Tao | 600/562 |
| 6,231,550 B1 | * | 5/2001 | Laughlin | 604/187 |
| 6,368,308 B1 | * | 4/2002 | Nerney | 604/227 |
| 6,719,735 B1 | * | 4/2004 | Gammon | 604/220 |

* cited by examiner

Primary Examiner—Nicholas Lucchesi
Assistant Examiner—Theodore J. Stigell
(74) Attorney, Agent, or Firm—Ronald E. Smith; Smith & Hopen, P.A.

(57) ABSTRACT

An adaptor for retrofit attachment to a syringe has a slide slideably mounted on the barrel of the syringe, a housing for releasably engaging a flange formed on the trailing end of the syringe plunger, an elongate connector for interconnecting the slide and the plunger housing, and a guide that releasably engages a flange formed at the trailing end of the barrel. Movement of the slide effects simultaneous and corresponding movement of the plunger. This allows a syringe operator to perform aspiration and injection in sequence with one-handed operation of the syringe. The slide is adjacent the leading end of the plunger so that the operator can see the leading end of the plunger. The user's fingers support the syringe from below. The flange housing permanently engages the flange in a second embodiment. In a third embodiment, the elongate connector and plunger are formed integrally at their respective trailing ends.

14 Claims, 7 Drawing Sheets

FORWARD-MOUNTED PLUNGER CONTROL FOR RETROFIT ATTACHMENT TO AN EXISTING SYRINGE

BACKGROUND OF INVENTION

1. Field of the Invention

This invention relates, generally, to syringes. More particularly, it relates to an attachment that is retrofit to a syringe to enable one hand operation and control of the position of the plunger from a point near a leading end of the syringe.

2. Description of the Prior Art

A conventional syringe structure includes a needle held at its base by a hub that is mounted at the leading end of a barrel. A plunger is slideably mounted in the barrel, and a piston having annular seals is provided at the leading end of the plunger. In a syringe used as an aspirator, withdrawal of the piston/plunger in a leading-to-trailing direction creates a vacuum in the leading end of the barrel that pulls liquid fluid into the barrel. In a syringe used for injection, displacement of the piston/plunger in a trailing-to-leading direction drives a liquid fluid out of the barrel and through the needle into the patient's tissue.

Some syringes are used for aspiration and injection. Thus, the plunger is retracted to accomplish aspiration, and thereafter advanced to accomplish injection. When a conventional syringe is used in this manner, the physician must develop a technique whereby the needle remains properly positioned during the retraction and the advancement of the plunger. The most common way of performing an aspiration is for the operator to hold the barrel in a first hand and to retract the piston/plunger with a second hand. For injection, the operator usually employs a one-handed technique. The operator steadies the barrel by holding two laterally-extending tabs at the trailing end of the barrel with the index and middle fingers and by using the thumb to advance the plunger in a distal-to-proximal (trailing-to-leading) direction in a well-known way.

There are occasions, however, when it is necessary to inject substances in a precise location, such as a vascular space. Any inadvertent injection of the substance outside its intended target may harm the patient. For example, in the practice of sclerotherapy, a caustic substance is injected into superficial, diseased veins to destroy them. The veins may be quite small and thin-walled and they are typically difficult to cannulate precisely with a needle tip. The patient experiences tissue destruction, ulceration and the pain concomitant therewith if the caustic substance is injected into tissue adjacent the diseased vein, so precision injection is a necessity. Accordingly, when performing an intravascular injection, the physician confirms needle tip location in the vascular space by aspiration until blood is seen. This requires retraction of the plunger. Injection, which requires advancement of the plunger, may then proceed.

The syringes now in use require the physician to change hand positions between the aspiration and the injection. Most physicians have developed their own personal techniques for controlling the plunger position with the same hand that holds the barrel of the syringe. These techniques include positioning a little finger on the trailing end of the plunger, holding the barrel in the palm of a hand so that the palm controls the plunger position, and other non-ergonomic techniques. The drawback of these techniques is that they require a high level of skill and cannot be repeated with consistency. Moreover, a change in hand position can lead to an accidental extravascular injection.

A number of syringes suitable for one-handed operation have been patented, but many of them are relatively complex in construction, difficult to use, and expensive to manufacture.

An earlier invention by the present inventor is believed to represent the most pertinent prior art to the present invention. That invention provides a syringe that can be controlled with one hand, but the novel mechanism is formed integrally with the syringe. Therefore, it does not compare favorably in price with conventional syringes because conventional syringes are made in very high quantities and thus are very inexpensive on a per syringe basis.

What is needed, then, is a low cost device that facilitates one-handed control during aspiration and injection that can be retrofit onto an existing syringe. The device should reduce the level of skill required for its use. Moreover, it should have a simple construction, be easy to use, easy to attach to an existing syringe of conventional construction, and should be economical to manufacture.

More particularly, a syringe attachment retrofittable to a conventional syringe is needed that enables sequential aspiration and injection with one hand in the absence of any need to change hand positions or to otherwise place the fingers, thumb or palm in an awkward position. The attachment would enable the operator to control the instantaneous position of the plunger with a single digit such as a thumb or a finger without requiring movement of any other part of the hand. This would provide more stability so that accurate injection into the proper space could be accomplished. The control point should be positioned forwardly, near the needle, to facilitate its use.

However, it was not obvious to those of ordinary skill in this art how the needed syringe could be provided, in view of the art considered as a whole at the time the present invention was made.

SUMMARY OF INVENTION

The long-standing but heretofore unfulfilled need for an innovation that overcomes the limitations of the prior art is now met by a new, useful, and nonobvious invention. The novel adaptor of this invention is easily attachable to an existing syringe of conventional construction. The syringe, with adaptor, is held and operated by a single hand. The operator of the syringe can perform aspiration and injection in sequence without changing hand position.

The construction of the existing syringe includes a needle, a hub for holding the needle, a barrel having a leading end to which the hub is mounted, an elongate plunger having a leading end slideably mounted within the barrel and a trailing end that is external to the barrel. A pair of laterally extending tabs is formed on the trailing end of the barrel and a flange is formed on the trailing end of the plunger.

The novel adaptor is manufactured separately from the syringe and is adapted to be releasably engaged thereto as a retrofit attachment. The novel adaptor includes a slide member that slideably engages an external, upper surface of the barrel. An elongate connector connects the slide member to the flange at the trailing end of the plunger. The slide member is adapted to be controlled by a thumb or finger of a user so that manipulation of the slide member controls an instantaneous position of the plunger.

The slide member is positioned at a leading end of the barrel, in closely spaced relation to the plunger so that the syringe operator can easily observe the respective positions of the slide member and the forward end of the plunger at the same time.

The slide member includes a first concave lower surface for slideably engaging the convex barrel and a second concave upper surface adapted for abutting engagement by a thumb or finger. The lower surface conforms to a curvature of the barrel and the upper surface is curved to provide an ergonomic support surface for a thumb or finger.

The connector that interconnects the slide member and the flange of the plunger is an elongate connector having a leading end formed integrally with the trailing end of the slide member and having a flange-engaging housing integrally formed therewith at a trailing end thereof. In a first embodiment, the flange-engaging housing releasably receives the flange formed on the trailing end of the plunger. In a second embodiment, the flange-engaging housing permanently engages said flange. The elongate connector is disposed in substantially parallel relation to the barrel.

The novel adaptor further includes a device that performs three functions. It releasably engages the laterally extending tabs formed on the trailing end of the barrel, slideably engages the elongate connector, and provides a handle means for the physician or other user when the syringe is in use.

In an alternative embodiment, instead of employing the flange-engaging housing that interconnects the elongate connector and the flange of the plunger, the elongate connector and plunger are formed integrally with one another. Thus, when the syringe is assembled by inserting the plunger into the hollow trailing end thereof, the slide member and the other parts of the novel assembly are simultaneously attached to the syringe structure.

It is a primary object of this invention to provide an adaptor for retrofitting onto a conventional syringe to facilitate the performing of one-handed aspiration and injection in sequence in the absence of any need to reposition the hand at any time.

Another object is to accomplish the foregoing object with a device constructed such that its use and method of operation are readily understood so that no training is required as a condition precedent to its use.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figures 1, 2:
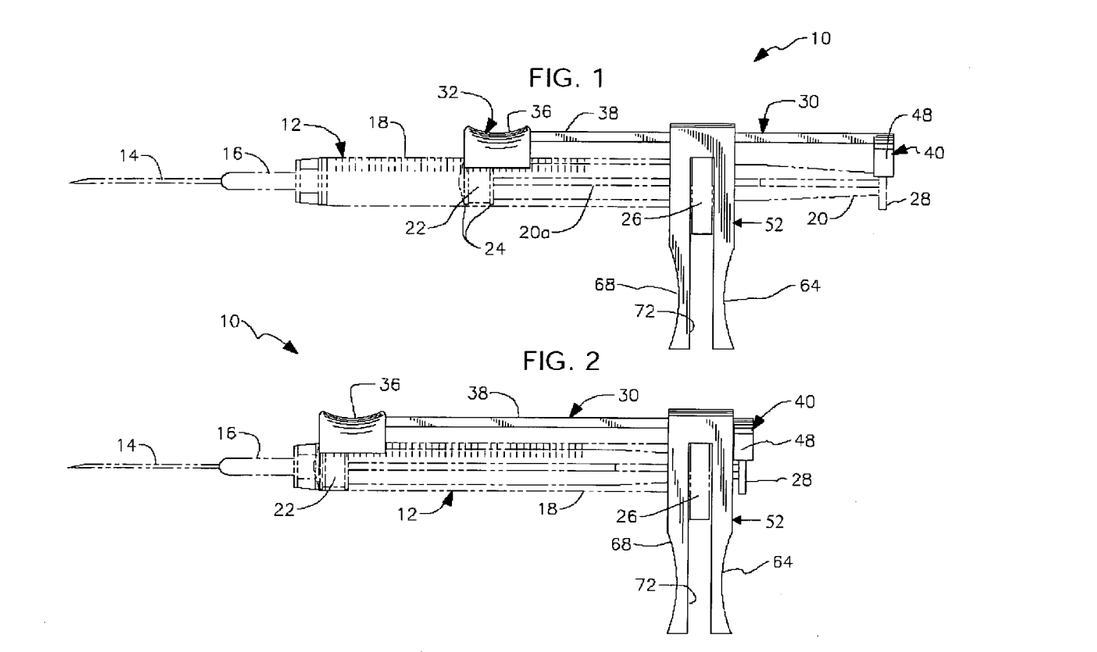
FIG. 1 is a side elevational view of a first illustrative embodiment of the invention when the plunger is in a rearward position.
FIG. 2 is a side elevational view of the first embodiment when the plunger is in a forward position.

Referring now to FIGS. 1 and 2, it will there be seen that an exemplary embodiment of the invention is denoted as a whole by the reference numeral 10.

Syringe 12 is depicted in phantom lines. It has a well-known, conventional construction. It is depicted with a retracted plunger in FIG. 1 and with an advanced plunger in FIG. 2.

Syringe 12 includes needle 14, hub 16, barrel 18, plunger 20, plunger rod 20a, and plunger head 22. Hub 16 is secured to the leading end of barrel 18 and holds the base of needle 14 in a well-known way. Plunger head 22 is sealed as at 24, so that liquid drawn into barrel 18 during aspiration does not leak therepast. The seal also prevents medication from leaking therepast when the syringe is used for injection.

A pair of laterally extending tabs 26 are integrally formed with barrel 18 at the trailing end thereof. Tabs 26, only one of which may be seen in the side elevational views of FIGS. 1 and 2, and barrel 18 collectively form a "T" shape when syringe 12 is seen in plan view. Flange 28 is provided at the trailing end of plunger 20.

In the absence of the novel syringe attachment, an injection is made with syringe 12 by placing two fingers on the leading or needle side of tabs 26 with barrel 18 between them, and a thumb pushes against plunger flange 28 to advance plunger head 22 in a distal-to-proximal (trailing-to-leading) direction. Plunger 20 and hence plunger head 22 cannot be retracted by retracting the thumb. A second hand is typically employed if it is desired to retract said plunger. Some nimble-fingered users may be able to retract the plunger by using a little finger, but such a technique requires a high level of skill and is not consistently reproducible with good results.

The novel apparatus is retrofit onto a conventional syringe and enables single-handed operation thereof. It is depicted in solid lines and is denoted 30 as a whole.

Figure 3:
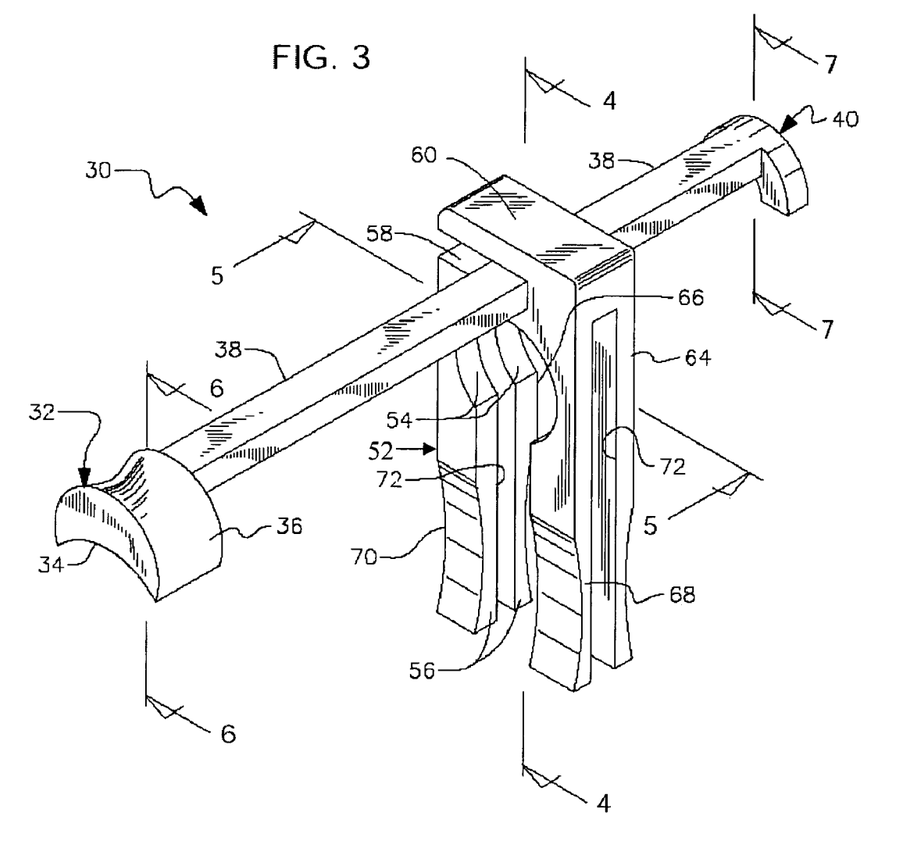
FIG. 3 is a perspective view of the novel device that is retrofit to a conventional syringe.
Figure 6:
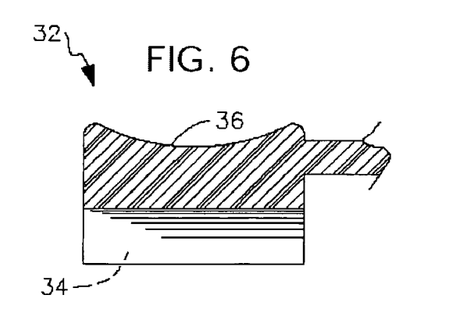
FIG. 6 is a sectional view taken along line 6—6 in FIG. 3.

Novel apparatus 30 includes slide member 32 that has a longitudinally-extending concave bottom surface 34 (see also FIGS. 3 and 6) that slideably engages the external surface of barrel 18.

Slide member 32 has an arcuate, saddle-shaped top surface 36 that is preferably ergonomically designed to comfortably support a thumb or finger. The preferred method of use of the novel apparatus is to position a thumb atop surface 36.

Elongate connector 38 has a leading end mounted to the trailing end of slide member 36.

Figure 7:
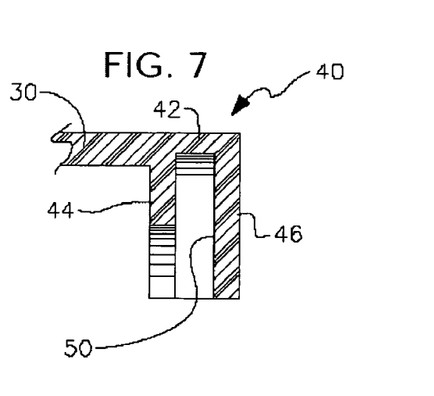
FIG. 7 is a sectional view taken along line 7—7 in FIG. 3.

Plunger flange 28 is formed integrally with plunger 20 at the trailing end thereof as aforesaid. In a first embodiment, it is releasably engaged by flange housing 40 formed integrally with the trailing end of elongate connector 30. As perhaps best understood in connection with FIG. 7, flange housing 40 includes a top wall 42, leading wall 44, trailing wall 46, side walls 48 (see FIGS. 1 and 2), and an open bottom, thereby creating a cavity 50 (FIG. 7) for receiving and capturing plunger flange 28.

Figure 4:
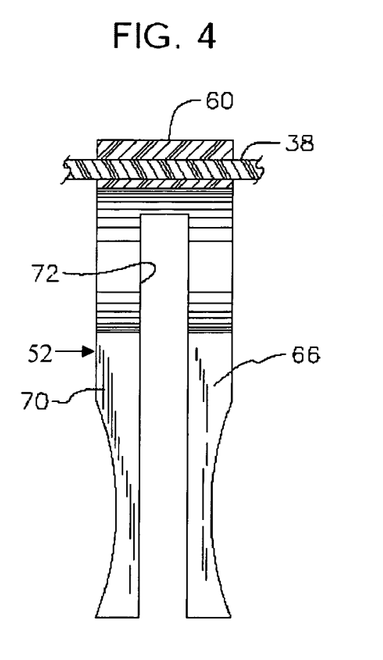
FIG. 4 is a sectional view taken along line 4—4 in FIG. 3.
Figure 5:
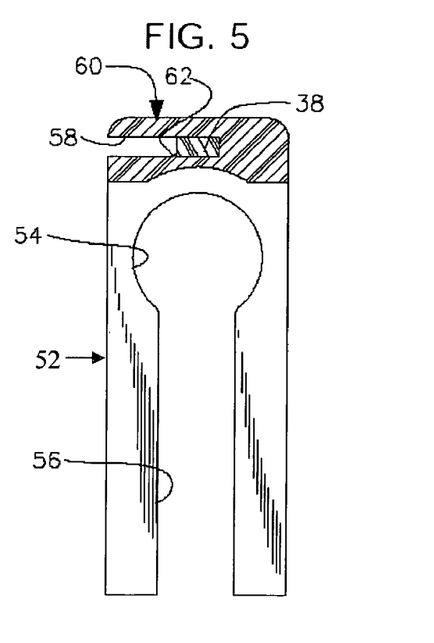
FIG. 5 is a sectional view taken along line 5—5 in FIG. 3.

Elongate connector 38 is maintained in spaced apart, substantially parallel relation to barrel 12 by guide 52. As best understood in connection with FIGS. 3–5, guide 52 includes a barrel 18-receiving opening 54 and a vertically extending slot 56 that slideably receives barrel 18 when guide 52 is snap fit thereonto. The diameter of barrel-receiving opening 54 is greater than the breadth of slot 56 so that barrel 18 is retained within said opening 54. Adaptor 30 is made of a flexible and resilient material, such as a plastic, so that slot 56 temporarily widens as barrel 18 approaches opening 54. Slot 56 thus returns to its position of repose, as depicted in FIG. 5, when barrel 18 is fully received within opening 54.

A horizontally extending slot 58 is formed in solid head 60 of guide 52 and said slot slideably receives elongate connector 38. Slot 58 is transversely disposed relative to a longitudinal axis of symmetry of syringe 12. Detent 62 retains elongate connector 38 within slot 58. When novel attachment 30 is assembled, the assembler feels and possibly hears a snapping action as elongate connector 38 is slid into slot 58 over detent 62 into its locked FIG. 7 position. Detent 62 is made of the same material as the rest of attachment 30 and thus has some flexibility and resilience so that elongate connector can be removed from its FIG. 7 position.

Guide 52 has a bifurcated construction below head 60. As best understood in connection with FIG. 3, leading legs 68, 70 are longitudinally spaced from trailing legs 64, 66, there being tab 26-receiving space 72 therebetween. Four legs 64, 66, 68, and 70 are created because barrel 18-receiving slot 56 intersects tab 26-receiving slot 72 at a right angle. Note that each of said four legs has an unnumbered concavity formed in its lower end. Specifically, the unnumbered concavities formed in trailing legs 64, 66 face the trailing end of attachment 30 and the unnumbered concavities formed in leading legs 68, 70 face the leading end of attachment 30. These concavities are ergonomic support surfaces for the user's fingers.

More particularly, a user grasps the syringe and attachment assembly 10 by placing a thumb against saddle-shaped surface 36 and by placing all four fingers under barrel 18 to support it from below. The trailing side of the middle finger may rest against the unnumbered concavities formed in the leading ends of legs 68, 70 and the leading side of the ring finger may rest against the unnumbered concavities formed in the trailing side of legs 64, 66. In the alternative, a user may prefer to position legs 64, 66, 68, and 70 between the index and middle fingers or between the ring and little fingers. With guide 52 so held, the thumb then pushes or pulls slide member 32 as required by the application. Note from FIGS. 1 and 2 that the location of slide member 32 and hence of the thumb is adjacent the location of plunger head 22. Accordingly, the user has a very intuitive as well as visual indication as to the instantaneous position of the plunger head.

Cradling apparatus 10 between the fingers and thumb in the manner described above is also an intuitive action. Thus, no training is required to learn how to use the novel apparatus.

The retrofit, snap-on attachment of adaptor 30 to conventional syringe 10 ensures simultaneous and corresponding movement of thumb-supporting surface 36 and the leading end 22 of plunger 20. No special skill is required to slide said slide member 32 rearwardly, i.e., in a distal-to-proximal or trailing-to-leading direction when aspirating blood into barrel 18, or forwardly, i.e., in a proximal-to-distal or leading-to-trailing direction when performing an injection. The forward and rearward sliding motion is a very simple motion that does not require the physician to re-grip the barrel or to otherwise re-position his or her hand during a procedure. Thus, the physician can pay maximum attention to proper needle location, and need not develop the skill of manipulating the trailing end of a plunger with a little finger or a palm of the same hand that holds the syringe.

Figure 8A:
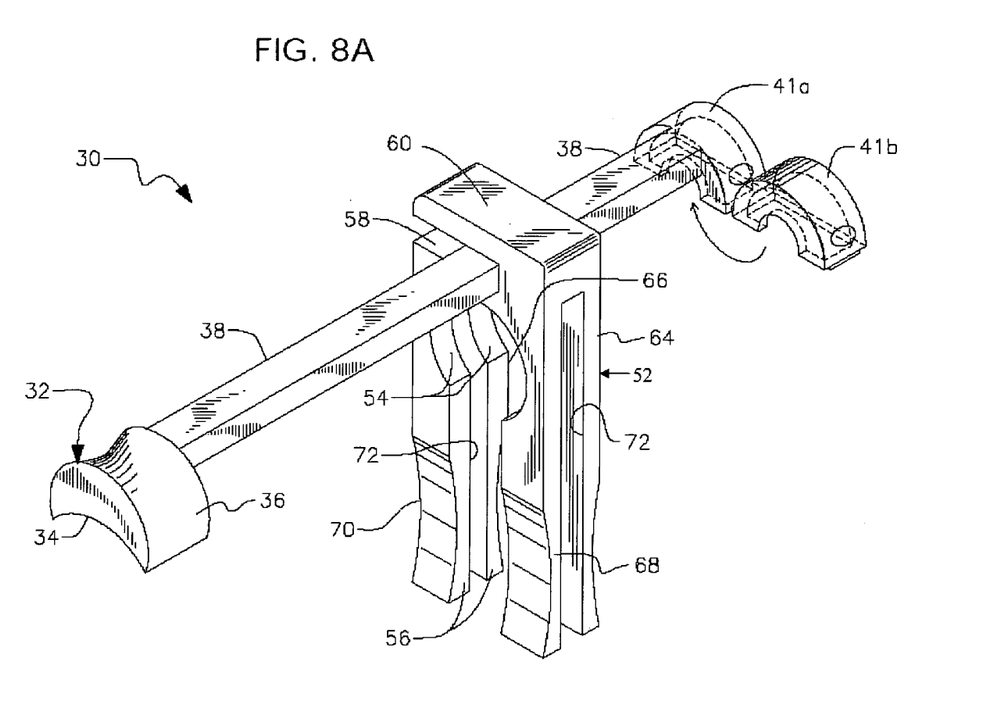
FIG. 8A is a perspective view of an alternative embodiment depicting a flange-engaging housing in an open configuration.
Figure 8B:
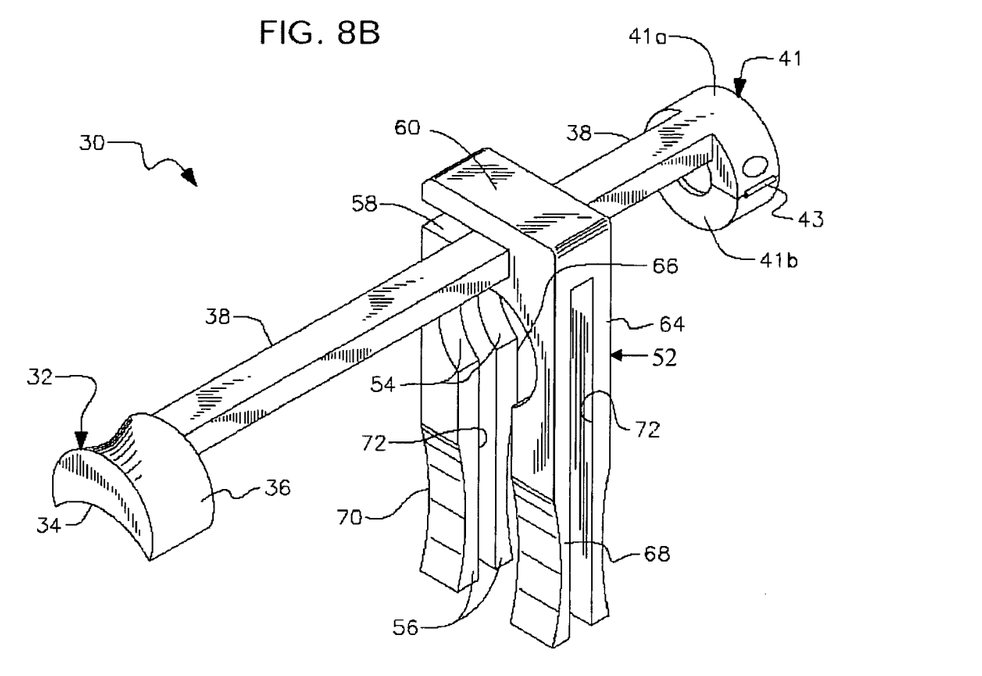
FIG. 8B is a perspective view depicting the flange-engaging housing of FIG. 8A in its closed configuration.

In a second embodiment, depicted in FIGS. 8A and 8B, flange housing 40 is replaced by flange-engaging housing 41 having a top half 41a and a bottom half 41b hingedly connected thereto by hinge 43 Said flange-engaging housing 41 is depicted in its open configuration in FIG. 8A, it being understood that said housing 41 must be open to receive flange 28. Said flange-engaging housing 41 is depicted in its closed configuration in FIG. 8B, it being understood that flange 28 would be captured therewithin in sandwiched relation between the top and bottom halves of said flange-engaging housing 41 when said housing is in its FIG. 8B configuration.

This second embodiment is used in the same way as the first embodiment, but flange-engaging housing 41 permanently engages flange 28, i.e., after top half 41a and 41b have been placed into their closed configuration, flange 28 is permanently housed therewithin because said half parts cannot be re-opened unless an extraordinary effort is made. There are numerous ways to lock said half parts together to prevent facile separation so the particular means employed is unimportant and for that reason is not depicted in detail. This second embodiment prevents a user from removing the novel assembly from one syringe to another.

Figure 9:
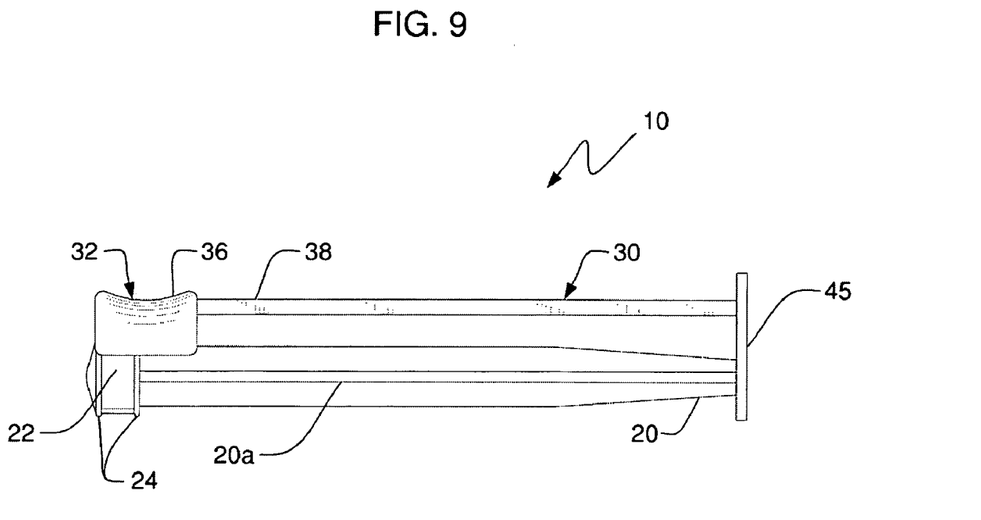
FIG. 9 is a side elevational view depicting an alternative embodiment where the elongate connector and plunger are formed integrally with one another.
Figure 10:
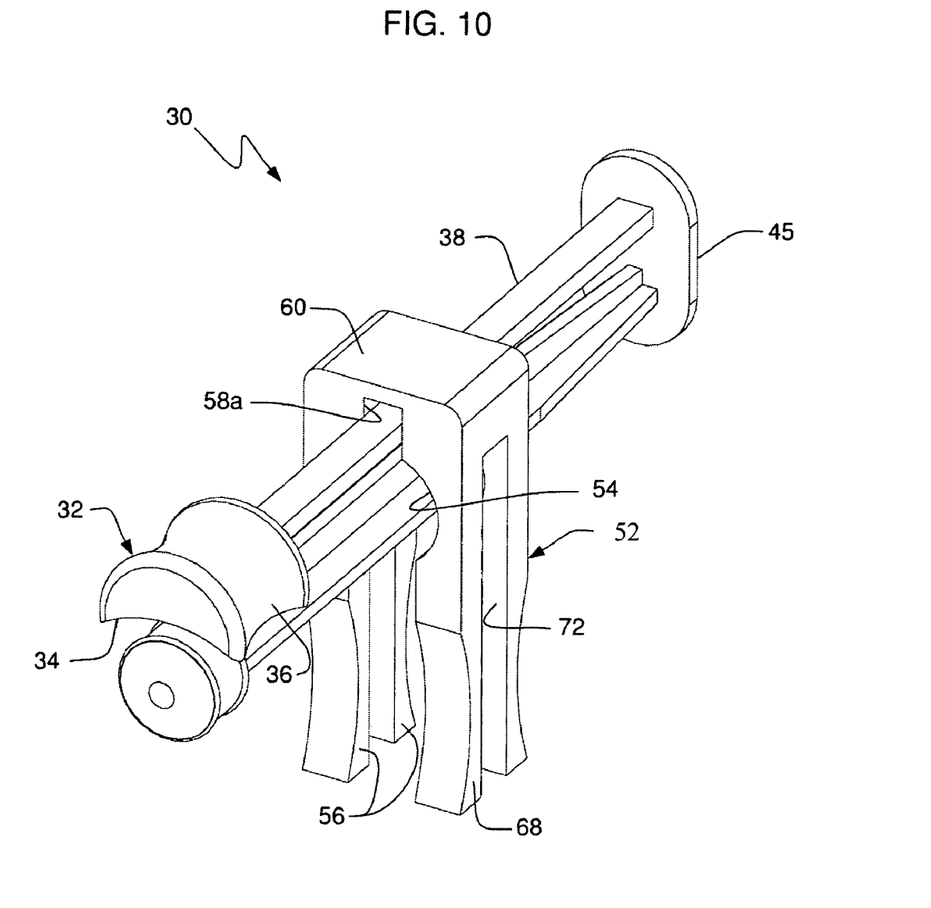
FIG. 10 is a perspective view of the guide member employed with the embodiment of FIG. 9.

A third embodiment is depicted in FIGS. 9 and 10. In this embodiment, elongate connector 38 is formed integrally with plunger 20. Specifically, the respective trailing ends of said parts are joined together by plate 45. This eliminates the need for flange-housing 40 of the first embodiment and flange-engaging housing 41 of the second embodiment. Note in FIG. 10 that slot 58a of guide 52 of this embodiment is vertically-extending, as distinguished from horizontally-extending slot 58 of the first two embodiments. In all other respects, the structure of this third embodiment is the same as the structure of the first two embodiments.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

The invention claimed is:

1. A forward-mounted plunger control adapter for retrofit attachment to a pre-existing syringe where the pre-existing syringe includes a needle, a hub for holding the needle, a barrel having a leading end to which the hub is mounted, a pair of laterally-extending tabs formed integrally with a trailing end of said barrel, an elongate plunger having a leading end slideably mounted within the barrel and a trailing end external to the barrel, said adaptor comprising:

a slide member adapted to slideably engage a first, upper surface of said barrel;

a flange housing adapted to releasably engage a flange formed integrally with a trailing end of said plunger;

an elongate connector for interconnecting said slide member to said flange housing so that movement of said slide member effects simultaneous and corresponding movement of said flange housing and hence of said plunger flange and hence of said plunger;

a guide member adapted to releasably engage said laterally-extending tabs;

said guide member adapted to releasably engage said barrel;

said guide member adapted to be grasped between fingers of a hand of a user;

said guide member being releasably and slideably engaged to said elongate connector;

said slide member adapted to be controlled by a digit of a user;

said slide member being positioned at a leading end of said barrel in closely spaced relation to a leading end of said plunger;

said slide member including a first, lower surface for slideably engaging said upper surface of said barrel and a second, upper surface adapted for continuous abutting engagement by a thumb or finger when said plunger is retracted in a leading-to-trailing direction and when said plunger is advanced in a trailing-to-leading direction;

whereby said syringe is adapted to be held in a single preselected hand when said adaptor is engaged thereto; and whereby no change in hand position is needed between a retraction of said plunger in a leading-to-wailing direction relative to said barrel and advancement of said plunger in a trailing-to-leading direction relative to said barrel.

2. The adaptor of claim 1, wherein said first lower surface conforms to a curvature of said upper surface of said barrel and wherein said second upper surface ergonomically conforms to the contour of a thumb or finger.

3. The adaptor of claim 1, wherein said syringe is supported from below by fingers of said user when in use; and wherein said guide member includes a plurality of legs that depend below said barrel and wherein said legs are positioned between preselected fingers of a user when the syringe is in use.

4. The adaptor of claim 3, wherein said plurality of legs is four legs, there being two leading legs positioned on opposite sides of said barrel and two trailing legs positioned on opposite sides of said barrel, and there being a space of predetermined longitudinal extent between said leading legs and said trailing legs.

5. The adaptor of claim 4, wherein said space of predetermined longitudinal extent is substantially equal to a thickness of the laterally extending tabs formed integrally with said trailing end of said barrel.

6. The adaptor of claim 1, wherein said guide member includes a solid head and a horizontally extending slot formed in said solid head, said horizontally extending slot adapted to slidingly receive said elongate connector, and said horizontally extending slot being transversely disposed relative to a longitudinal axis of said syringe.

7. The adaptor of claim 6, further comprising a detent means formed in said horizontally extending slot to retain said elongate connector within said horizontally extending slot.

8. The adaptor of claim 1, wherein said guide member further comprises:

a head for engaging said elongate connector;

a first pair of legs depending from opposite sides of said head and being positioned on opposite sides of said barrel for engaging said barrel therebetween;

a second pair of legs depending from opposite sides of said head and being positioned on opposite sides of said barrel for engaging said barrel therebetween; and said first pair of legs being longitudinally spaced from said second pair of legs by a predetermined longitudinal extent.

9. The adaptor of claim 8, wherein said predetermined longitudinal extent is substantially equal to a thickness of said laterally extending tabs.

10. A syringe attachment adapted to be retrofit onto a syringe including a needle, a hub for holding the needle, a barrel having a leading end to which the hub is mounted, a pair of laterally extending tabs formed integrally with a trailing end of said barrel, an elongate plunger having a leading end slideably mounted within the barrel and a trailing end external to the barrel, a flange formed integrally with said trailing end of said elongate plunger, comprising:

said slide member having a first, lower surface that slideably engages a first, upper surface of said barrel and a second, upper surface that supports a finger or a thumb;

a flange housing adapted to engage said flange formed integrally with said trailing end of said plunger;

an elongate connector for interconnecting said slide member to said flange housing so that movement of said slide member effects simultaneous and corresponding movement of said flange housing and hence of said flange and hence of said plunger;

a guide member adapted to engage said laterally extending tabs;

said guide member adapted to engage said barrel;

said guide member adapted to be grasped between fingers of the hand of a user;

said guide member being releasably and slideably engaged to said elongate connector;

said slide member adapted to be controlled by a digit of a user;

said slide member being positioned at a leading end of said barrel in closely spaced relation to a leading end of said plunger;

whereby said attachment is adapted to be attached to said syringe;

whereby said syringe is adapted to be held in a single preselected hand when said attachment is engaged thereto; and whereby no change in hand position is needed between a refraction of said plunger in a leading-to-trailing direction relative to said barrel and advancement of said plunger in a trailing-to-leading direction relative to said barrel.

11. The syringe attachment of claim 10, wherein said guide member includes a solid head and a horizontally extending slot formed in said solid head, said horizontally extending slot adapted to slidingly receive said elongate connector, and said horizontally extending slot being transversely disposed relative to a longitudinal axis of said syringe.

12. The syringe attachment of claim 11, further comprising a detent means formed in said horizontally extending slot to retain said elongate connector within said horizontally extending slot.

13. The syringe attachment of claim 10, wherein said guide member further comprises:
- a head for engaging said elongate connector;
- a first pair of legs depending from opposite sides of said head and being positioned on opposite sides of said barrel for engaging said barrel therebetween;
- a second pair of legs depending from opposite sides of said head and being positioned on opposite sides of said barrel for engaging said barrel therebetween; and
- said first pair of legs being longitudinally spaced from said second pair of legs by a predetermined longitudinal extent.

14. The syringe attachment of claim 13, wherein said predetermined longitudinal extent is substantially equal to a thickness of said laterally extending tabs.

* * * * *